United States Patent [19]

Engelbrecht et al.

[11] 4,248,232
[45] Feb. 3, 1981

[54] METHOD OF DISSOLVING THE BOND BETWEEN INTERCONNECTED COMPONENTS

[76] Inventors: Eckart Engelbrecht, Andreasstr. 33, Hamburg; Elmar Nieder, Hinterdeich 117, Jork, both of Fed. Rep. of Germany

[21] Appl. No.: 941,661

[22] Filed: Sep. 12, 1978

[30] Foreign Application Priority Data

Sep. 13, 1978 [DE] Fed. Rep. of Germany ....... 2741107

[51] Int. Cl.³ ............................................. A61B 17/32
[52] U.S. Cl. ...................................... 128/305; 3/1.91;
29/426.4; 83/13; 128/24 A; 128/92 E; 156/344;
264/23; 264/36; 433/86

[58] Field of Search .................. 156/344, 584; 29/427,
29/426.4; 128/1 R, 24 A, 303 R, 303.1, 303.14,
305.1, 305, 92 R, 92 E, 92 EC; 264/23, 36;
433/86; 3/1.9, 1.91; 83/13; 30/272 A

[56] References Cited

U.S. PATENT DOCUMENTS

| 2,742,076 | 4/1956 | Klein | 29/427 |
| 3,401,446 | 9/1968 | Obeda et al. | 156/344 X |
| 3,683,736 | 8/1972 | Loose | 264/25 X |
| 3,809,977 | 5/1974 | Balamuth et al. | 128/24 A X |

Primary Examiner—John T. Goolkasian
Assistant Examiner—Thomas Bokan
Attorney, Agent, or Firm—Spencer & Kaye

[57] ABSTRACT

An ultrasonic tool is used for dissolving the bond between nested components cemented together by a plastic layer. The vibrating tool causes softening of at least portions of the plastic layer, and subsequently the components can be readily detached from one another.

4 Claims, 6 Drawing Figures

METHOD OF DISSOLVING THE BOND BETWEEN INTERCONNECTED COMPONENTS

BACKGROUND OF THE INVENTION

The invention relates to a method for dissolving the bond between interconnected (nested) components which, together with a plastic layer which bonds them together, form a compound system. The method effects configurational changes in the system. The invention moreover relates to an apparatus for performing the method.

Compound systems of structural components which are nested together with the aid of a cement-like plastic layer (hereafter also referred to as "synthetic material") are used in many technological fields, provided that the surfaces of the components can be so designed that the connecting plastic can effect a form-locking connection with these parts. In particular, such techniques are used for components which cannot be connected in any other manner since they are in accessible, for example, either to welding or riveting. In most cases the components are of unlike materials.

A very significant field of application for such compound systems is the field of endoprostheses which is concerned with the connection of members of a living organism with artificial prostheses. In surgical operations on bones or joints, a bone cement (e.g. a methylmethacrylate) is used to fix alloplastic substitute joints, for compound osteosyntheses, for example, in the field of neurosurgery for dorsal cervical vertebra reinforcements and for cranial replacements. The bone cement connects the metallic or nonmetallic implant with the bone by way of clamping profiles on the prosthesis on the one hand to roughnesses and protrusions on the bone on the other hand.

In many cases it is necessary to exchange or align an endoprosthesis. The procedure of exchanging the endoprosthesis is effected by first exposing the joint in question. Then the prosthesis and which generally still resists mechanical removal - although it might have already become loosened to the point of being painful - is freed of surrounding bone cement by reshaping the bone, if necessary, whereupon a new prosthesis is implanted with bone cement. In alloplastic surgery on joints it is the practice to remove as little bone as possible when implanting a prosthesis and to encase the prosthesis in as much bone and soft tissue as possible so that only the functionally required part remains exposed. The entire anchoring is generally effected in a closed cylindrical (tubular) bone. Thus, this bone must remain intact as much as possible when the prosthesis to be exchanged is removed so as to permit implantation of a new prosthesis. This involves the difficulty that the bone cement must be removed from very narrow gaps, sometimes only a few millimeters in width, by means of long special chisels, cutters and drills. Often it is necessary to fenestrate the bone at locations more remote from the joint. Only after the endoprosthesis connection has been freed sufficiently from the cement-like plastic layer can the prosthesis be tapped out and the operation be continued. After removal of the endoprosthesis, the surgical field becomes larger and any residual bone cement still remaining in the marrow cavity can be removed with chisels, cutters and drills or by screwing cement parts to thread cutters and knocking them out. If necessary, the bone is reshaped and then a new endoprosthesis is implanted with bone cement.

Compound osteosyntheses are bone reconstructions involving a combination of plates, nails, wires, screws and bone cement. Such surgical procedure is relied upon for bone fractures where mere reconstruction by means of the above-described metal parts is insufficient and it is necessary to additionally support the bone by means of bone cement. In the neurosurgical field, reinforcements are employed particularly for the cervical vertebrae if there is a threat of slippage of the vertebrae with respect to one another and thus there is a danger of damage to the spinal cord. The prothesis of the vertebrae are tied together with wires, the cavities between the prothesis and the wires are filled with bone cement. In principle, this is a compound osteosynthesis. Parts of the cranium are replaced by cement-like plastics. After insertion of the replacements to be implanted, it is necessary to conform the shape of the surrounding area with mechanical tools. In order to permit tissue outside the artificial cranium to grow together with tissue inside it, the artificial cranium must be perforated at numerous places. Additionally it is possible to neurosurgically replace a vertebra by means of bone cement. However, there exists no satisfactory stabilization between the individual artificial vertebrae and between the artificial vertebrae and the remaining healthy vertebrae.

Exchanging or aligning an endoprosthesis is generally a complicated and very time consuming procedure. The difficulty resides in the fact that during removal of the endoprosthesis the bone should not be injured. Even with the greatest of care bone is often damaged and thus the secure seat of the new endoprosthesis is endangered and reconstructive measures may become necessary. Intentionally applied bone fenestrations may weaken the bone to a degree which is no longer justifiable.

Exchange operations are time consuming and may require many hours. The stress from anesthesia is considerable, particularly since the patients are usually old. During the long surgical procedure the loss of a considerable amount of blood from the marrow cavity cannot be prevented. Blood transfusions up to 5 liters are no rarity. This may produce grave postoperative complications and, for example, coagulation problems in the patient which then constitute a mortal danger. The great loss and transfusion of blood and the long operating times in these operations which require very large personnel are a considerable cost factor.

Dorsal reinforcements performed in neurosurgery on cervical vertebrae sometimes require correction. The connecting parts, bone cement and wires, may come loose or break, or the reinforcement may have to be extended to further sections of the spinal column. In such an operation, the previously applied wire and bone cement must be removed. The removal with mechanical tools, such as chisels, cutters and drills is again time consuming and, particularly in the immediate vicinity of the spinal cord, dangerous because of resulting jarring or the possibility of one of the tools slipping.

Cranial replacements of plastic must be reshaped once the plastic has hardened and has been implanted. This process is very time consuming when conventional tools are employed. Jarring may endanger the firm seat of the implant.

SUMMARY OF THE INVENTION

It is an object of the present invention to improve a process and an apparatus of the above-mentioned type so that working on the cement-like plastic layer between the two nested components is substantially simplified without damaging the components or changing their composition.

This is accomplished by the present invention by effecting changes in shape with the aid of vibrations in the ultrasonic range.

The influence of ultrasound makes the synthetic material plastic in the boundary layer adjoining the object excited with ultrasonic waves so that the object can be moved from its position with respect to the synthetic material, whereby changes in shape are made in the cement-like synthetic material. The latter is worked with the aid of ultrasound so that it can be removed from the interstice between the nested components. This application of the invention is particularly useful in surgical procedures as outlined above. The described operations on bones and joints are substantially simplified. The probability of a far-reaching protection of tissues to be preserved - particularly the bone - increases considerably. The risk during the exchange of alloplastic substitute joints is reduced since renewed secure support and anchoring of the new implant is assured if the bone substance is essentially protected during the removal of the old implant. Moreover, the length of the operations is reduced considerably because the removal of bone cement with the aid of ultrasonically excited tools can be accelerated considerably. This eliminates long periods of anesthesia which, as noted before, could endanger the patient. Moreover, the patient is protected in that heavy blood losses are avoided. Shortening the time of the operation also has a saving influence on the costs for personnel and materials.

According to a preferred embodiment of the invention, an apparatus for practicing the method is designed as an ultrasonically excited tool which has a shape that enhances changes in shape of the compound system. With such design it is assured that at the tip of the tool a great amount of energy is available which serves to loosen the synthetic material and which, due to the special design of the tool, can easily be transmitted to such material to change it in the desired manner. Thus the tool can penetrate quickly into the synthetic material without the user of the tool having to exert considerable forces. Then the material is removed so that the components can be separated.

DESCRIPTION OF THE PREFERRED EMBODIMENTS

The method according to the invention is based on the recognition that a great number of thermoplastic materials, for example polymethylmethacrylate, are heated locally in the boundary layer between the tool and the plastic when being worked with tools that vibrate in the ultrasonic range. As a result of the heating, the plastic melts and thereafter hardens again. During the plastic intermediate phase the object which has been excited in the ultrasonic range, for example the tool, changes its position with respect to the plastic and thus has a form-changing influence on the plastic. For example, if a component embedded in the plastic layer is excited in the ultrasonic range, the boundary layer of the component melts, so that the position of the component can be changed as long as the boundary layer remains plastic due to the excitation of the component. The component thus can be taken out of the plastic layer.

Figure 5:
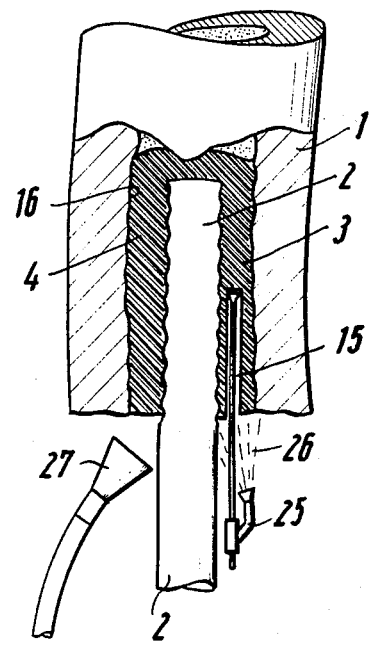
FIG. 5 is a sectional view of a connection of two components by means of plastic.
Figure 6:
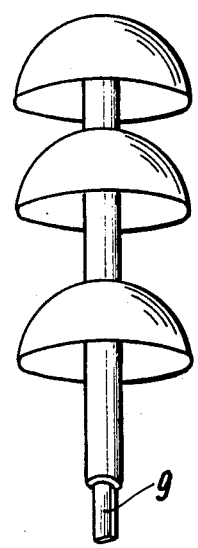
FIG. 6 is a perspective view of a profiled tool.

If instead of the component an ultrasonically excited tool is introduced into the synthetic layer, the tool penetrates into the plastic or liquid boundary layer formed between the synthetic material and the tool as a result of the ultrasonic excitation of the tool. The tool prevents the plastic from repolymerizing after the excitation has been discontinued. In this way, the tool makes a path for itself through the plastic material so that the latter is, by the path, separated into several parts. After the tool has worked several paths in the plastic, the pieces of plastic disposed between the paths can be removed from the interstice 3 disposed between components 1, 2 (FIG. 5).

A similar procedure is employed if in a medical case, for example, an endoprosthesis must be exchanged. It would be conceivable in this case to connect the prosthesis, which can be perceived as the internal component 2, directly with a sonotrode 6 of an ultrasonic device 5. In this case it is important to provide as rigid a connection as possible between the sonotrode 6 generating the ultrasonic vibrations and the endoprosthesis so that the largest amount of vibratory energy possible is introduced into the endoprosthesis by the sonotrode 6. This connection may be established, for example, with the aid of a screw connection 7 which is provided at the tip of the sonotrode 6. The screw connection 7 is screwed to a shaft 8 which is provided with a corresponding thread. It is also possible to employ a sleeve nut. Moreover, any other rigid connection between the sonotrode 6 and the prosthesis to be loosened is possible. A similar connection may additionally be provided for coupling other tools to the sonotrode 6.

By exciting the endoprosthesis in the ultrasonic range, the boundary layer of the plastic layer 4 melts along the interfaces with the shaft protruding into the plastic layer 4. In this state the endoprosthesis 2 can be removed from the cavity of the bone 1.

Figure 3:
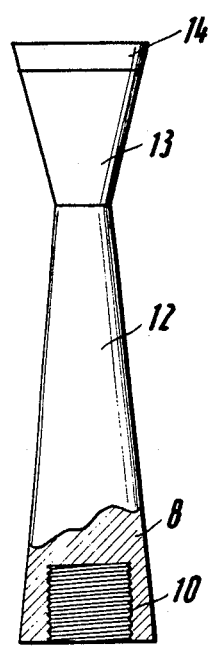
FIG. 3 is a side view of a chisel.

The endoprosthesis may also be removed from the tubular bone by completely removing the plastic layer 4 surrounding the endoprosthesis. For this purpose, another tool is placed onto the sonotrode 6 with the aid of which the bone cement, formed as the plastic layer 4, is removed from the interstice 3. Such a tool may be, for example, a chisel 12 (FIG. 3) which may be provided with a shaft 8 at its end facing the sonotrode 6. At its opposite end a cutting head 13 with a cutting edge 14 is provided which penetrates into the bone cement when the chisel 12 is excited in the ultrasonic range. Upon penetration, the tool leaves a path 15 in the plastic layer 4. A plurality of such paths 15 may thus be worked into the bone cement so that between the paths loose plastic parts are formed which can be removed from the interstice 3. Once the endoprosthesis 2 has been substantially loosened, it can be tapped out of the cylindrical bone. Remaining fragments of the bone cement may remain attached to the inner walls 16 of the bone (FIG. 5). These fragments can be removed quickly and thoroughly, after removal of the endoprosthesis, with the use of tools excited in the ultrasonic range since there now is available sufficient room in the cylindrical bone to use such tools. It is then also possible to introduce ultrasonically excited connecting elements, such as, for example, thread cutters, self-cutting screws or other profiled tools, into the remaining plastic until they have been firmly connected therewith. Then, by applying appropriate forces to these tools, the remainder of the plastic can be removed from the cylindrical bone by breaking, pulling or chiseling. For this purpose, on the shaft 8 appropriate coupling devices are provided to which the appropriate forces can be applied. For example, at the shaft 8, a square coupling 9 can be provided for applying a torque thereto. It is also possible to fasten an abutment plate 28 to the shaft 8 for transmitting a striking energy or pulling forces to the tool.

Figure 1:
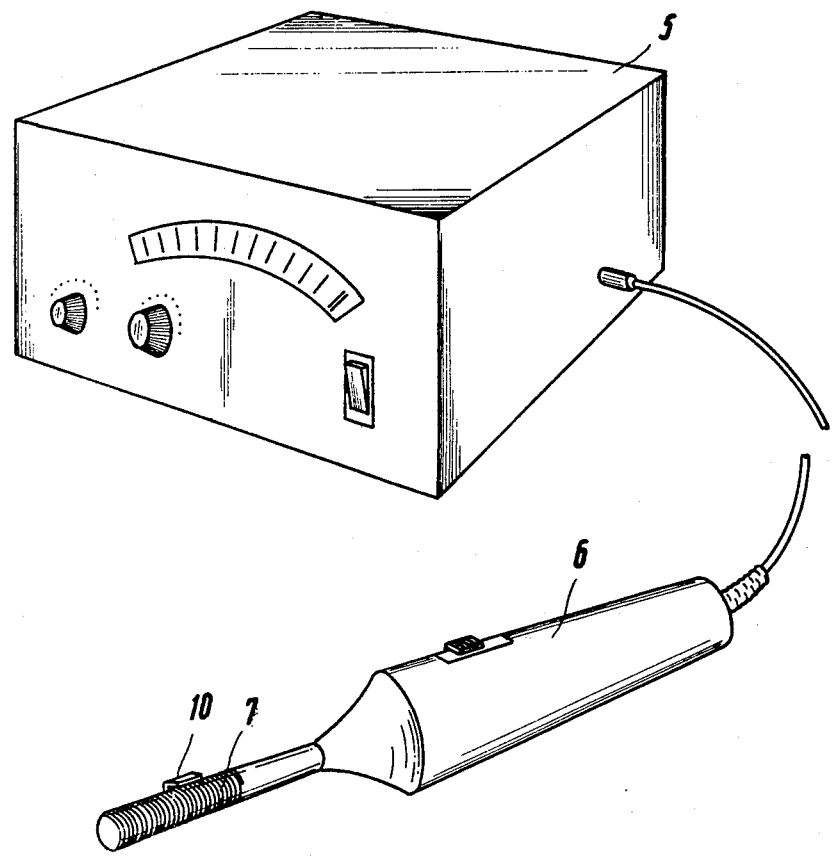
FIG. 1 is a perspective view of an ultrasonic device with connected sonotrode.
Figure 2:
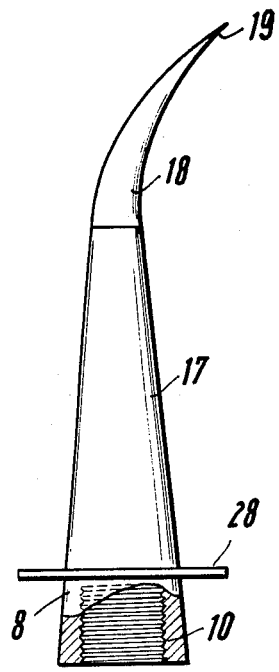
FIG. 2 is a side view of a tool designed as a scraper.

For further simplification of the work, the sonotrode 6 may be provided with other interchangeable tools. It is conceivable, for example, to design a scoop 17 (FIG. 2) which is placed onto the sonotrode 6. This scoop is provided, at its end remote from the sonotrode 6, with a shallow, spoon-like curvature 18. The curvature 18 is slightly inclined to the side with respect to the direction of the shaft 8 which is to be connected with the sonotrode 6 so that loosened remainders of plastic may collect in the corner zone between the spoon-like curvature 18 and the shaft 8 and can be scraped out of the interstice 3. The inclination is held within the limits which permit optimum energy transfer from the tip of the spoon to the plastic. At its end 19 the spoon-like curvature 18 comes to a relatively sharp point so that the spoon-like curvature 18 can easily penetrate into the plastic layer 4. With the aid of this scoop 17, relatively broad paths can be worked into the plastic layer 4 and the loosened plastic can be removed.

Figure 4:
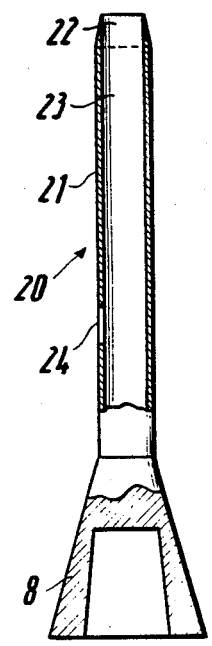
FIG. 4 is a side view of a hollow tool.

A further tool that may be mounted on the sonotrode 6 is a hollow probe 20 (FIG. 4) which has, at the end of the shaft facing away from the sonotrode 6, a thin tubule 21. This tubule is excited in the ultrasonic range and its open end 22 is pressed into the bone cement. The softened bone cement then travels up the cavity 23 in the tubule 21. After the tubule 21 is filled, the hollow probe 20 is pulled out of the bone cement and the core of plastic is removed from the cavity 23. It is also conceivable to provide a window 24 in the wall of the tubule 21 through which the bone cement traveling up the cavity 23 is continuously extruded.

The removal of the plastic core from the tubule 21 can be simplified by providing the interior of the tubule with a polished surface from which the plastic core slides off with ease. The inner walls of the tubule 21 may be cone-shaped, widening from the open end 22 in the direction toward the shaft 8. The plastic core will then easily slide out of the tubule 21 at its wider open end 22.

Further, a vacuum device may be connected to window 21 to continuously extract the plastic during use of the tool. On the tubule 21a pressure may be applied to facilitate its penetration into the plastic. It is conceivable to press the plastic core out of the tubule 21.

Advisably, the wall of the tubule 21 is honed to form a cutting edge at its end 22 to facilitate penetration of tubule 21 into the plastic. With such a hollow probe it is also possible to work paths into the plastic layer 4 quickly and cleanly. In this way, the plastic layer can be divided into a plurality of individual parts which can be removed from the interstice 3, for example by means of the scoop 17.

Additionally, the cutting edges of all tools may have, e.g. a sawtooth shape. This ensures that upon vibrations in the ultrasonic range, a particularly intensive cutting effect takes place at the protrusions, e.g. at the tips of the sawteeth.

All tools that may be mounted on the sonotrode 6 have the advantage that they are small and convenient, making possible a penetration even into narrow interstices 3. The tools have a thickness of only a few millimeters, but may be up to 300 mm long, without causing a significant energy loss along the tool to its tip.

It is thus possible with the aid of these tools to remove bone cement even from the usually inaccessible places between implant and bone. With a small cold light source 25 (FIG. 5) which can be fastened, for example, on the shaft 8 or on the sonotrode 6, a focused beam of light 26 is guided in the direction toward the point where the tool is being used. It illuminates the field of the operation so that the surgeon can always guide the tool into the correct direction. In this way it is possible to remove the bone cement, even at inaccessible places, easily, quickly, without shock and thus without damage to tissue and particularly to bone tissue. In addition, in the immediate vicinity of the operating field, a suction device 27 may be provided with the aid of which the gases as well as blood and wound secretions developing during working of the plastic can be extracted. Thus the field of the operation will always be kept free of impurities and the surgeon will retain a good field of view.

In the compound system, nonmetallic prosthesis parts, which may be duraplastics, can also be worked on directly with the above described tools. Thus these prosthesis parts can be removed quickly so that the operating field is enlarged accordingly and the interior of the cylindrical bone can be cleaned quickly and neatly of any remaining fragments.

It is possible, within the scope of compound osteosyntheses, to connect metallic materials with the soft bone cement while it is still in the hardening phase or to encase them in such bone cement. Improperly inserted nails and plates can be disengaged with the aid of ultrasonic tools, for re-insertion at a different location. It is feasible to couple the metallic osteosynthesis parts directly to the sonotrode 6 and removed from the bone cement.

When replacing vertebrae with artificial members, the artificial vertebrae formed of bone cement are shaped during the operation to conform to the anatomy and are placed into their position. Then the artificial vertebrae are fused to each other and to the healthy vertebrae to conform to the individual anatomy. If further artificial vertebrae need be implanted at a later date, the older compound system can be loosened with the aid of ultrasonically excited tools and can be replaced by a new one.

Moreover, the method of the invention can be used for working on prostheses in the area of the cranium. For example, bone cement can be shaped to replace the top of the cranium so as to repair possible damage to the top of the cranium. After filling up the damaged portions, it is generally necessary to subsequently mechanically shape the prosthesis to adapt it to the remaining bone substance. The mechanical adaptation and shaping results in jarring of the skull which endangers the firm seat of the implant. With the aid of ultrasonic tools, such work can be performed essentially without jarring; thus, these tools can be used to perform subsequent work without endangering the success of the operation.

It is to be understood that the above description of the present invention is susceptible to various modifications, changes and adaptations and the same are intended to be comprehended within the meaning and range of equivalents of the appended claims.

We claim:

1. In a method of dissolving the bond between an artificial prosthesis component and a bone of a patient wherein the component projects into a bone cavity and is embedded into a plastic bone cement bonded to the bone and to the component such that a space is maintained between the component and inner wall faces of the bone; the improvement comprising the following steps:
   (a) vibrating a tool in the ultrasonic range;
   (b) contacting the plastic bone cement with the vibrating tool for at least locally softening the plastic bone cement;
   (c) introducing the vibrating tool into said plastic bone cement in said space whereby a path is cut by the vibrating tool in the plastic bone cement;
   (d) repeating the contacting and introducing steps for providing a plurality of paths;
   (e) removing plastic bone cement portions from between said paths for weakening the bond; and
   (f) subsequent to step (e), removing said component from said cavity.

2. A method as defined in claim 1, further comprising the step of forcing melted plastic bone cement from the paths into a channel of the tool simultaneously with step (c) and emptying the plastic from the tool channel.

3. A method as defined in claim 1, wherein step (e) comprises the step of removing parts of said plastic bone cement with the vibrating tool.

4. In a method of dissolving the bond between an artificial prosthesis component and a bone of a patient, wherein the component projects into a bone cavity and is embedded into a plastic bone cement bonded to the bone and to the component such that a space is maintained between the component and inner wall faces of the bone; the improvement comprising the following steps:
   (a) vibrating a tool in the ultrasonic range;
   (b) contacting the plastic bone cement with the vibrating tool for at least locally softening the plastic bone cement;
   (c) introducing the vibrating tool into said plastic bone cement in said space;
   (d) subsequent to step (c), discontinuing the vibration of the tool while it is in an inserted state in the plastic bone cement;
   (e) subsequent to step (d), allowing the softened plastic bone cement to solidify and adhere to said tool;
   (f) subsequent to step (e), removing said tool from said cavity together with the plastic bone cement adhered thereto; and
   (g) subsequent to step (f), removing said component from said cavity.

* * * * *